United States Patent
Palamand et al.

[11] Patent Number: 5,178,327
[45] Date of Patent: Jan. 12, 1993

[54] AIR FRESHENER

[75] Inventors: Shashi Palamand; S. Rao Palamand, both of St. Louis County, Mo.

[73] Assignee: Summit Products, Inc., St. Louis, Mo.

[21] Appl. No.: 739,401

[22] Filed: Aug. 2, 1991

[51] Int. Cl.⁵ ............................................. A61L 9/12
[52] U.S. Cl. ..................................... 239/57; 239/60; D23/366
[58] Field of Search ....................... 239/34, 57, 60, 52; D23/366, 367, 368, 369

[56] References Cited

U.S. PATENT DOCUMENTS

| | | | |
|---|---|---|---|
| D. 252,706 | 8/1979 | Schimanski | 239/57 X |
| 2,103,609 | 12/1937 | Bradburn | 239/59 X |
| 2,555,047 | 5/1951 | Logue | 239/57 X |
| 2,608,436 | 8/1952 | Baughman | 239/47 |
| 3,410,488 | 11/1968 | Sugimura | 239/326 X |
| 3,711,023 | 1/1973 | Smith | 239/55 X |
| 3,908,905 | 9/1975 | Von Phillip et al. | 239/57 X |
| 4,094,639 | 6/1978 | McMillan | 239/60 X |
| 4,603,030 | 7/1986 | McCarthy | 239/60 X |
| 4,865,816 | 9/1989 | Walz et al. | 239/60 X |
| 4,921,636 | 5/1990 | Traas | 239/60 X |

Primary Examiner—Andres Kashnikow
Assistant Examiner—William Grant
Attorney, Agent, or Firm—Polster, Lieder, Woodruff & Lucchesi

[57] ABSTRACT

An air freshener includes container which carries a cartridge having a plurality of sections, each of which is filled with a porous material impregnated with a differently scented substance. At least the front wall of the container has an aperture of generally the same shape and size as the cartridge sections. The cartridge may be rotated within the container to selectively bring one of its sections into alignment with the aperture, in order to expose a scented substance in one of the sections to the ambient air contained within a room, causing evaporation of the scented substance and freshening of the room's air. The back wall of the container may also be provided with an aperture, which is in general axial alignment with the front wall aperture, and tape or the like surrounding the aperture, so that the air freshener may be mounted over a vent or the like. In this manner, the fragrant scent will be spread into a room by force rather than by convection.

7 Claims, 1 Drawing Sheet

AIR FRESHENER

BACKGROUND OF THE INVENTION

This invention relates to air fresheners, and in particular, to an air freshener carrying a plurality of scents, any one of which may be selected by a single action such as rotating or dialing.

Many people place air fresheners in a room to cover up odors in the room or just to add a fragrant scent to the air. Many air fresheners are commercially available. However, most of these provide for only one scent. Sometimes people want to change the scent introduced into a room. With commercially available air fresheners, the only way to do this is to purchase another air freshener having a different scent.

A few air fresheners which allow a user to selectively alter the scent delivered by the freshener have been described. For example, U.S. Pat. No. 3,711,023 to Smith discloses an air freshener having a plurality of shells which may be selectively opened and closed and which are positioned in front of a fan. Each shell carries numerous cells which contain fragrant compounds. Each shell has a different scent. The fan blows air through the cells of each shell causing the fragrant compound to evaporate and to be carried into the room. By opening and closing the various shells to varying degrees, the scent delivered by the air freshener can be altered.

U.S. Pat. No. 3,410,488 to Sugimura discloses an air freshener having a plurality of atomizing units. Each unit has a container of perfume which, when activated by an electrical signal, sprays its perfume through an atomizer and onto a strip of porous material. Each strip moves in front of its own fan which evaporates the perfume and carries it into the room. By changing the frequency of when the various perfume containers are activated, the scent created by the air freshener may be altered.

U.S. Pat. No. 2,608,436 to Baughman discloses a vaporizer having a plurality of vials of scented liquid positioned behind a fan. The vials can be selectively opened and a wick, which reaches into the liquid, can be extended to draw the liquid into the air flow. By selectively opening the vials, the scent which is delivered can be altered.

Lastly, U.S. Pat. No. 2,103,609 to Bradburn discloses an air freshener having a body which carries a plurality of open topped vials of scented substances. A cover is rotatably mounted on the body to seal and close the vials. The cover has an opening which can be selectively brought into alignment with any one of the vials to open the vial, to allow the substance within the vial to evaporate and freshen the air.

All but the last mentioned patent are electrically operated and thus require a source of electricity. All have the disadvantage of being complicated and bulky. They are not easily moved nor can they be easily placed in a room out of view.

SUMMARY OF THE INVENTION

One object of this invention is to provide an air freshener which will permit a user to select a desired fragrance.

Another object is to provide such an air freshener wherein the fragrant substance may be replaced when used up.

Another object is to provide such an air freshener which may be mounted over a vent or the like.

Another object is to provide such an air freshener which is small so that it can be placed in small rooms or in cars.

Another object is to provide such an air freshener which is also economical to produce and easy to use.

Other objects will become obvious to those skilled in the art in light of the following disclosure and accompanying drawings.

In accordance with the invention generally stated, an air freshener is provided. The air freshener includes a container preferably including an openable top, a front wall, a back wall, side walls, and a bottom. A cartridge is rotatably and removably mounted in the container. The cartridge has a hub, an outer wall, and vanes extending between the hub and the outer wall to define sections. At least the front wall and preferably both the front and back walls of the container each have an aperture shaped and dimensioned to be the same size as each section. The cartridge is removably mounted on an axle which extends through the container and has an exposed knob attached to one end. The axle can be rotated to selectively bring one of the sections into alignment with the apertures. The sections each contain a scented substance. Each section carries a differently scented substance. The sections are sealed within the container and preferably against the front and back walls to prevent the scents from the different substances from mixing together.

DESCRIPTION OF THE PREFERRED EMBODIMENT

Figure 1:
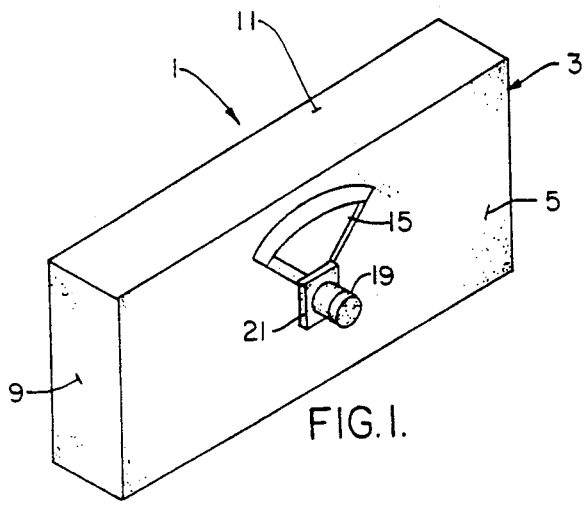
FIG. 1 is a perspective view of an air freshener constructed in accordance with the teachings of the present invention.
Figure 2:
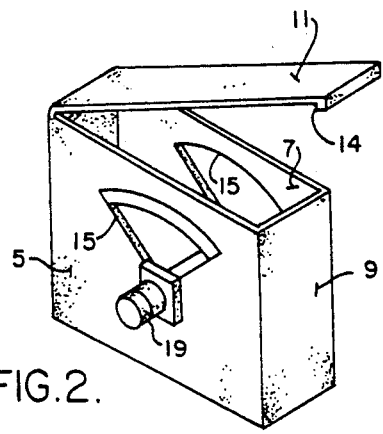
FIG. 2 is a perspective view of a container of the air freshener with the top of the container partially opened.

Referring to the drawings, an air freshener 1 of the present invention includes a container 3 preferably having a front wall 5, a back wall 7, side walls 9, a top 11, and a bottom 13. As seen in FIG. 2, top 11 is hingedly connected to one of the side walls 9 and may be selectively opened and closed. Top 11 has a downwardly extending lip 14 at its free end. Lip 14 engages and covers the outside of one of the sidewalls 9 to hold top 11 closed. Front and back walls 5 and 7 each have an aperture 15 which are axially aligned with each other. An axle 17 having a knurled knob 19 is journaled through the front and back walls below apertures 15, 15. Front wall 5 has an opening 20 through which the axle 17 extends. Back wall 7 may have a sleeve (not shown), mounted to its inner surface opposite to and in axial alignment with hole 20, which rotatably receives axle 17 to support axle 17 within container 3. Front wall 5 may have a journal box 21 thereon through which the axle extends. Knob 19 is positioned outside of wall 5 so that it may be used to rotate axle 17.

Figure 3:
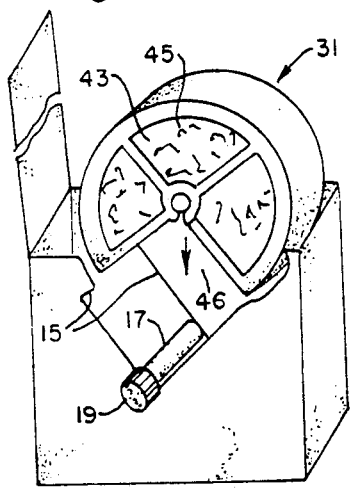
FIG. 3 is a perspective view of the air freshener container, partly broken away, with its top open and a cartridge containing fragrant substances being inserted therein.
Figure 4:
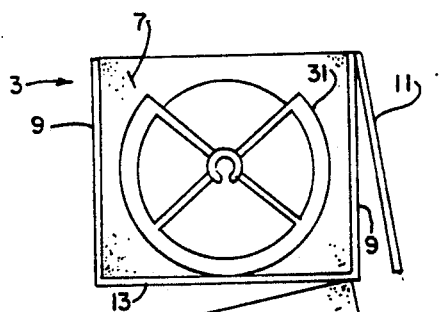
FIG. 4 is a front elevational view of the air freshener with a front panel removed therefrom showing the cartridge placed therein.
Figure 5:
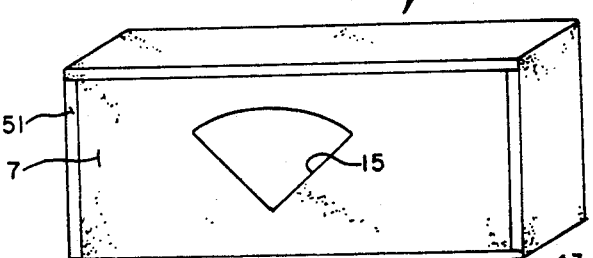
FIG. 5 is a perspective view of the air freshener showing a back side thereof.
Figures 6, 7:
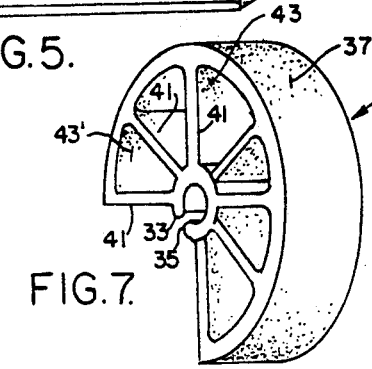
FIG. 6 is a front elevational view of the cartridge.
FIG. 7 is a perspective view of another embodiment of the cartridge.
Figure 8:
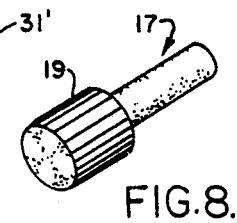
FIG. 8 is a perspective view of an axle on which the cartridge is mounted.

A cartridge 31 is removably received in container 3. cartridge 31 includes a hub 33 and an outer circular wall 37. Hub 33 is not continuous and has a gap 35 therein. Wall 37, like hub 33, is not continuous and has a beginning 39 and an end 40 defining a gap 42 which allows access to hub gap 35. A plurality of vanes 41 extend between hub 33 and outer wall 37 to separate the cartridge into a plurality of sections 43. In FIGS. 3, 4 and 6, cartridge 31 is shown as having four segments. In FIG. 7, cartridge 31' has several more sections 43'. Sections 43 and 43' are filled with a porous material 45 which is impregnated with a volatile fragrant substance. In FIGS. 3 and 6, all but one of the sections are filled with porous material 45, leaving a blank section 46 which is defined by two vanes which intersect the beginning 39 and end 40 of outer wall 37. The blank section 46 corresponds to the gap 42 in outer wall 37. The various sections 43 are filled with differently scented substances. Material 45 fully fills each section 43 and may be frictionally held or adhesively secured therein. Alternatively, the inside of outer wall 31 may have projections or other means which extend into the material 45 to hold it in place.

Hub gap 35 is just wide enough so that cartridge 31 may be removably snapped onto axle 17. Thus, when the scented substances in the cartridge 31 evaporate, a new cartridge 31 can be placed in its stead. Hub 33 has a diameter sized so that cartridge 31 will be rotatably fixed to axle 17 for rotation therewith when rotated by knob 19. The front and back apertures 15, 15 in walls 5 and 7 are of the same shape and dimension as sections 43 and are positioned so that one section 43 may be brought into alignment with the apertures 15, 15. Thus the scented substance in a selected section 43 can be exposed so that it will evaporate to freshen a room's air. Section 46 can also be brought into alignment with apertures 15 so that no air freshening occurs. Section 46 is also preferably of the same size as sections 43.

Vanes 41 have gaskets or the like on opposite sides so that sections 43 are sealed against the inside of walls 5 and 7 to keep the fragrance of the various sections from mixing together. If desired, two sections 43, 43 can be exposed through apertures 15, 15 so that the fragrance of the sections mix as the fragrant substance evaporates.

In FIG. 7, alternate sections 43' of cartridge 31' may be left empty. This enables the amount of the scented substance that enters the air to be varied, by varying the amount of the section that is exposed. Of course, the cartridge 31' can also alternatively be filled with a greater variety of scented substances to give the user more choices. It will be apparent that when cartridge 31' is used, apertures 15, 15 must be made smaller than when the apertures 15, 15 which are used with cartridge 31.

The back 7 of container 3 may have a tape strip 51 or the like extending around the outer edge of back wall 7 so that the container 3 may be secured around a vent opening. This allows the fragrance in the selected section 43 to be forced into a room, rather than by convection alone. A small fan, operable by a battery or line electricity, may be mounted on the back of the device to push air therethrough, if desirable. Tape 51 need not be used to secure container 3 to a vent. For example, hook and pile fasteners such as Velcro may be used.

Numerous variations, within the scope of the appended claims, will be apparent to those skilled in the art in light of the foregoing description and accompanying drawings. Although the cartridge is shown to be round, it may be any shape desired, so long as it can rotate within container 3. The edge of the outer wall 37 can be marked above each section to display the name of the scent carried therein. Top 11 may be hingedly connected to any of the sides. Further, it need not be the top that is opened. Any side con be opened so long as the cartridge can be removably mounted on axle 17. If the front or back were to open, the axle could be square or rectangular in cross-section and the hub would be shaped complementarily thereto and could be slid on and off the axle. The use of a faceted or non-circular axle and hub would prevent any slippage between the hub and the axle due to friction between the cartridge and the container. Rather than the sections being filled with an impregnated porous material, the sections could be filled with evaporating substances, as are common in air fresheners. This may require the use of wires or strings which pass through the substance to hold it in the section as it evaporates and becomes smaller. Alternatively, the front and back walls of the cartridge may be provided with mesh like material which would assist in holding the fragrance material inside each segment of the cartridge. These examples are merely illustrative, and are not meant to be restrictive in interpreting the present invention.

Having thus described the invention, what is claimed and desired to be secured by Letters Patent is:

1. An air freshener comprising:
   a self-supporting and enclosed container;
   a cartridge rotatably and removably mounted in said container, said cartridge having an annular hub, an outer wall, and vanes extending between said hub and said outer wall and defining a plurality of sections, each said section carrying a differently scented substance;
   said container having at least one wall which includes an aperture that is generally shaped and dimensioned to the same size as each said section; and
   axle means received by said hub for selectively rotating said cartridge to bring a selected section into alignment with said aperture to expose a scented substance in one of the sections to ambient air; said axle means being exposed so as to be rotatable.

2. The air freshener of claim 1 further including at least one section which contains no scented material.

3. An air freshener comprising:
   a self-supporting and enclosed container, said container including means for mounting said air freshener over a source of moving air in order to force air through said container;
   a cartridge rotatably and removably mounted in said container, said cartridge having a hub, an outer wall and vanes extending between said hub and said outer wall and defining a plurality of sections, each said section carrying a differently scented substance;
   said container including front and back walls each having apertures generally shaped and dimensioned to the same size as each said section; and
   means for selectively rotating said cartridge to bring a selected section into alignment with said apertures to expose the scented substance in said selected section to said source of moving air.

4. An air freshener comprising:

a self-supporting and enclosed container;

a cartridge rotatably and removably mounted in said container, said cartridge having a hub, an outer wall and vanes extending between said hub and said outer wall and defining a plurality of sections, each said section carrying a differently scented substance;

said container having at least one wall which includes an aperture that is generally shaped and dimensioned to the same size as each said section;

means for selectively rotating said cartridge to bring a selected section into alignment with said aperture to expose a scented substance in one of the sections to ambient air; and an axle journaled in front and back walls of said container, said cartridge including means for removably mounting said cartridge on said axle, said rotating means comprising an exposed knob connected to said axle which rotates said axle when rotates, and said cartridge being rotatably fixed to said axle.

5. The air freshener of claim 4 wherein said mounting means includes a gap in said hub accessible through a gap in said cartridge outer wall, said hub gap being constructed such that said hub can be pressed and snapped onto said axle as well as pulled and snapped off said axle.

6. An air freshener cartridge for use in an enclosed container and including an annular hub and vanes extending radially from said hub to an outer wall and defining a plurality of sections; said sections being filled with differently scented substances which will impart their scents into the air; and axle means received by said hub for selectively exposing said sections to the atmosphere outside said container, said axle means being exposed so as to be rotatable.

7. The air freshener of claim 6 further including at least one section which contains no scented substance.

* * * * *